United States Patent [19]

Stevens et al.

[11] Patent Number: 4,829,608
[45] Date of Patent: May 16, 1989

[54] SHOWERS

[76] Inventors: Sean Stevens; Mark Smith, both of 18 Grand Boulevard, Montmorency, 3094, Victoria, Australia

[21] Appl. No.: 131,492
[22] Filed: Dec. 10, 1987

[30] Foreign Application Priority Data

Dec. 10, 1986 [AU] Australia .................... PH09428

[51] Int. Cl.⁴ .............................................. A47K 3/22
[52] U.S. Cl. ........................................ 4/597; 4/612; 4/614; 128/395; 128/396; 250/494.1; 312/223
[58] Field of Search ................ 34/4; 4/524, 596, 597, 4/598, 605, 607, 612, 613, 614; 128/366, 367, 395, 396, 362, 371; 250/493.1, 494.1, 504 R; 312/12, 132, 273, 223

[56] References Cited

U.S. PATENT DOCUMENTS 4,444,189 4/1984 Seiverd ........................... 128/371

Primary Examiner—Henry J. Recla
Assistant Examiner—J. Casimer Jacyna
Attorney, Agent, or Firm—Sughrue, Mion, Zinn, Macpeak & Seas

[57] ABSTRACT

A shower incorporates a translucent wall, and behind the wall is mounted an assembly of lamps for directing ultraviolet radiation into the shower so as to tan the occupant. The lamps are mounted on a frame which may be withdrawn from behind the wall by movement along tracks, so as to permit replacement of the lamps.

9 Claims, 4 Drawing Sheets

SHOWERS

BACKGROUND OF THE INVENTION

The present invention relates to showers.

It has been proposed to incorporate into a shower infra red and/or ultraviolet radiation sources. Such an arrangement is disclosed in U.S. Pat. No. 4,424,598, DE No. 3,500,367, DE No. 331,740, GB No. 2,020,970, AU No. 252,062. All of these prior proposals are, however, unsatisfactory as regards the general mounting of the radiation sources and the provision for access to permit replacement and servicing whilst maintaining the sources sealed from the shower.

SUMMARY OF THE INVENTION

According to the present invention, there is provided, in combination, a shower wall having a translucent panel, an assembly behind the panel, said assembly including at least one lamp for emitting ultraviolet radiation into the shower via the panel, and means mounting said assembly for movement generally parallel to the wall to permit the assembly to be withdrawn from behind the wall at least to an extent sufficient to permit replacement of the or each lamp.

BRIEF DESCRIPTION OF THE DRAWINGS

An embodiment of the invention will now be described, by way of example only, with reference to the accompanying drawings, in which.

DETAILED DESCRIPTION OF THE INVENTION

Figure 1:
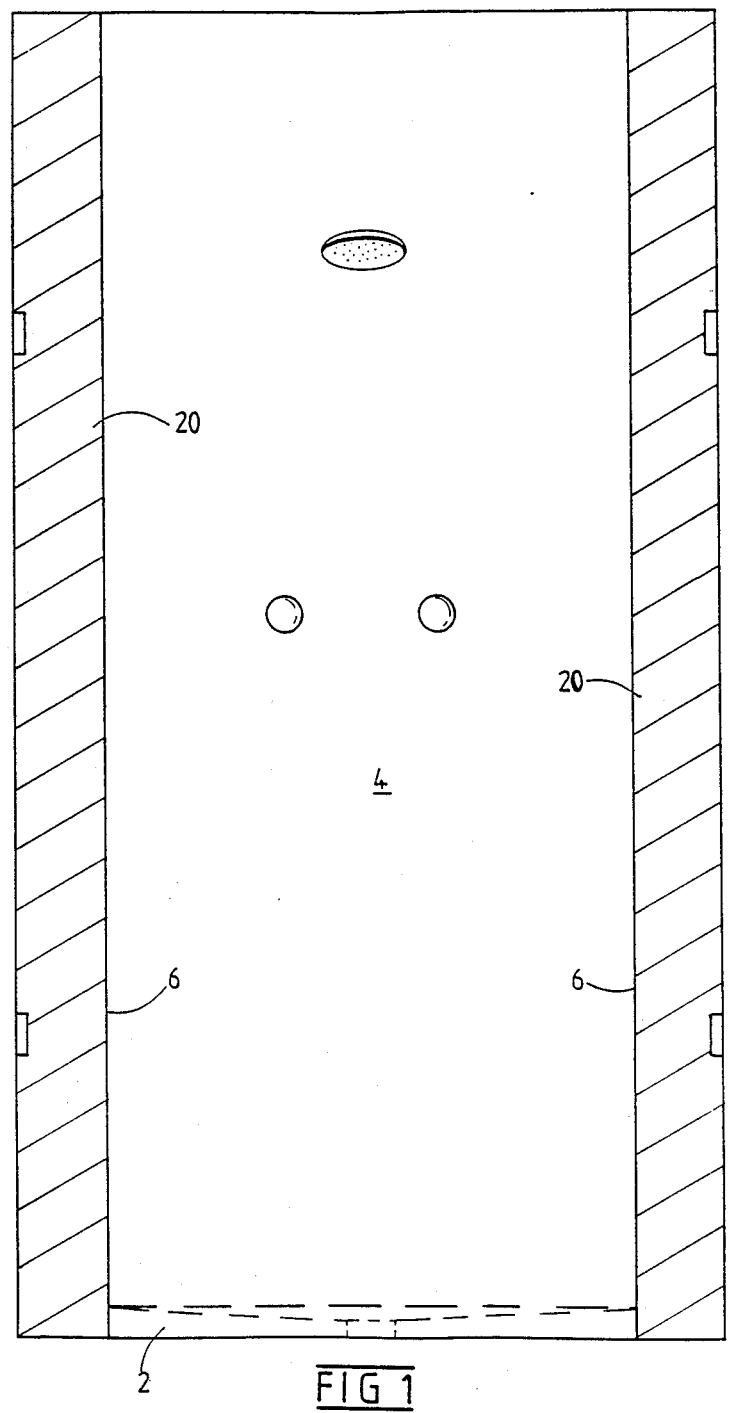
FIG. 1 is a front elevation of a shower incorporating an assembly for emitting ultraviolet radiation.
Figure 2:
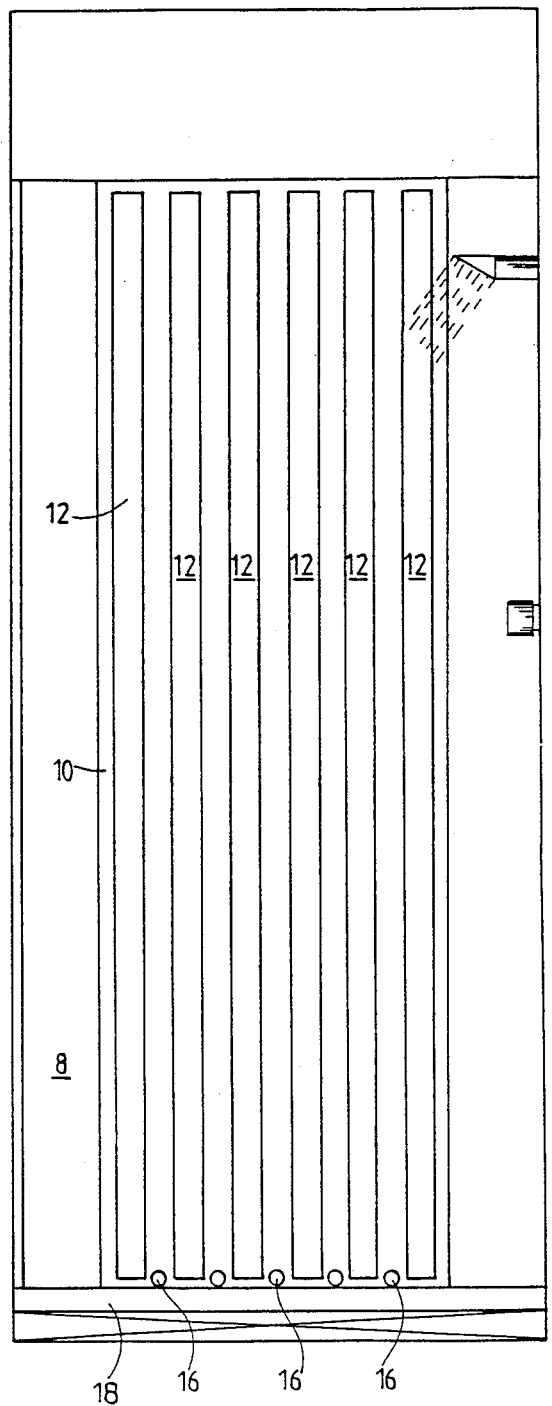
FIG. 2 is an elevation of one of the assembly as installed.
Figure 3:
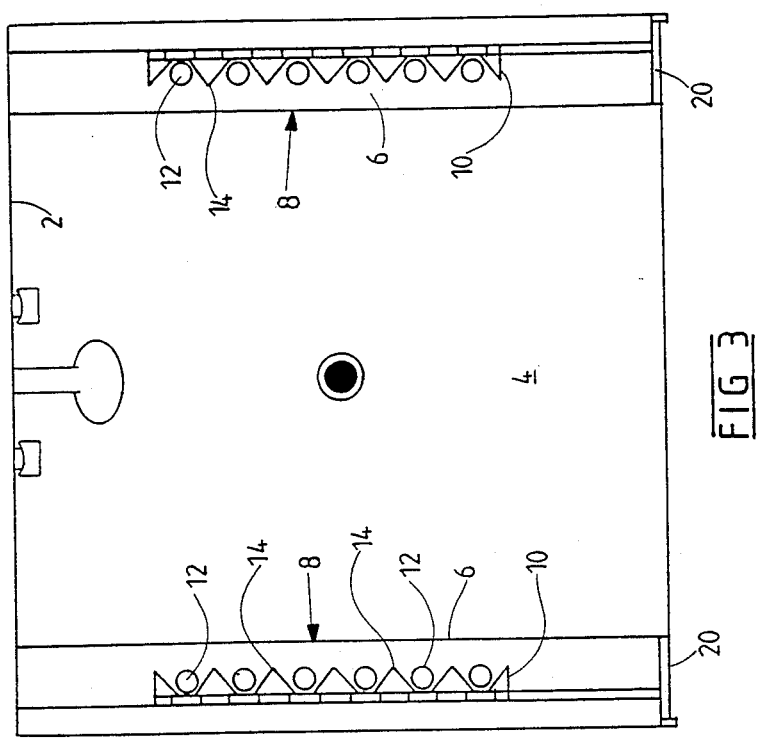
FIG. 3 is a plan view of the shower.

As shown in the drawings, a shower assembly comprises a tray 2, a rear wall 4 and opposed side walls 6. Each side wall 6 is of hollow construction and comprises a transparent, waterproof, inner panel 8, for example of acrylic sheet such as "Perspex", which faces into the interior of the shower. The interior of the side wall 6 houses, behind the transparent panel 8, a frame 10 supporting an array of ultraviolet lamps. Preferably, the lamps are in the form of parallel fluorescent tubes 12 which extend vertically in the frame, and span substantially the entire height of the side wall 6, the array of lamps extending across a substantial part of the width of the side wall. The frame 10 also carries reflectors 14 positioned to reflect light into the interior of the shower.

The frame 10 is supported at its lower edge on wheels 16 which run along a horizontal track 18 in the base of the side wall 6, the frame also being suitably guided or supported at its upper edge. The frame 10 can be withdrawn, at least partly from the interior of the wall 6 via an open front edge of the wall 6, by movement along the track 18. In its withdrawn position the frame 10 is exposed to permit easy replacement of the lamps. Suitable guide means (not shown) are provided for locating and guiding the upper part of the frame, while the frame 10 is located within the wall, and when the frame is withdrawn from the wall. A hinged or other movable end panel 20 closes the open front edge of the side wall in order to enclose the frame 10 in the side wall, suitable sealing means being provided between the end panel 20 and the side wall to ensure that no water enters the interior of the side wall when the end panel is in position to close the front edge.

Figure 4:
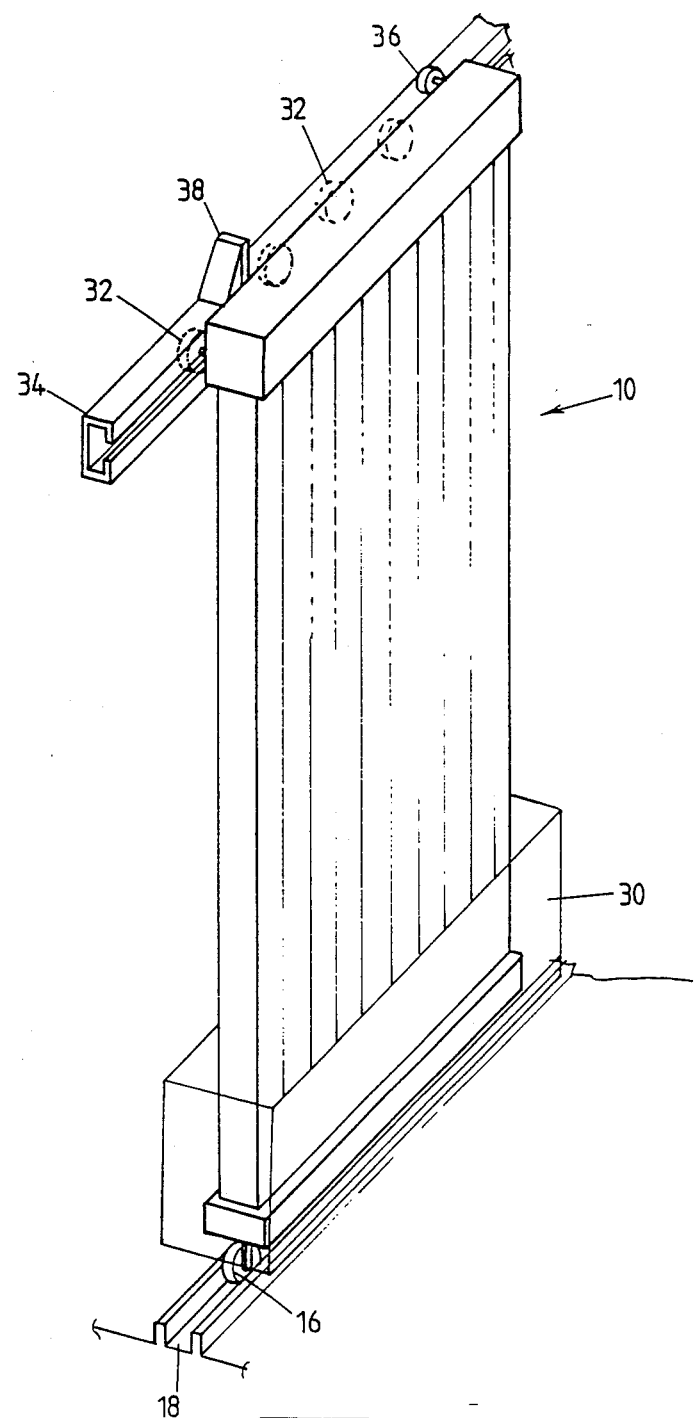
FIG. 4 is a perspective view of an especially preferred form of the assembly.

In an especially preferred arrangement as shown in FIG. 4, the frame 10 includes at its bottom a box-like casing 30 which is open at the top and which shields the lower ends of the lamps and associated electrical equipment against water which may penetrate behind the shower wall and rise to the level of the lower ends of the lamps. The casing 30 carries the wheels 16 (typically, four such wheels) which are spaced along the length of the casing to run along the track 18. At its upper end, the frame carries a row of wheels 32 (again, typically four such wheels) which project laterally from the frame to engage in a horizontal guide track 34 secured to the adjacent wall of the overall recess in which the shower is installed. A stop wheel 36 externally of the track 34 is operative to engage a stop 38 carried by the upper side of the track 34 at a position corresponding to a desired extent of maximum withdrawal of the frame. In this withdrawn condition, the frame is exposed to an extent sufficient to provide ready access to the lamps so as to permit replacement of the lamps, while the frame is still supported by the tracks 18, 34.

Operation of the lamps 12, while a person is showering, results in emission of ultraviolet radiation to cause tanning of the person over his entire body. The lamps used are chosen to emit radiation substantially wholly within the ultraviolet band of the spectrum, with substantially no emission of infra red radiation and which would cause excessive heating within the interior of the hollow side walls.

The invention may be embodied within an integral pre-formed shower comprising the sidewalls, rear wall and tray which can be installed, as a unit, in a suitable recess. Alternatively hollow, prefabricated side wall assemblies incorporating the frames and lamps, can be produced for installation into existing showers or for building-in into new showers constructed on site.

The embodiment has been described by way of example only and modifications are possible within the scope of the invention.

We claim:

1. In combination, a shower wall having a translucent panel, an assembly behind the panel, said assembly including at least one lamp for emitting ultraviolet radiation into the shower via the panel, and means mounting said assembly for movement generally parallel to the wall to permit the assembly to be withdrawn from behind the wall at least to an extent sufficient to permit replacement of the or each lamp.

2. A combination according to claim 1, wherein the assembly is supported for rectilinear movement substantially parallel to the plane of the wall.

3. A combination according to claim 1, wherein the assembly is supported for movement along guide tracks adjacent upper and lower ends of the assembly.

4. A combination according to claim 3, comprising means for limiting the extent to which the assembly can be withdrawn along the tracks.

5. A combination according to claim 1, comprising means defining an opening adjacent the front of the shower and through which the assembly may be withdrawn, and a door for closing the opening when the assembly is in its operative position behind the panel.

6. A combination according to claim 1, wherein the assembly comprises a plurality of tubular lamps extending substantially vertically.

7. A combination according to claim 6, wherein the assembly comprises means protecting the lower ends of the lamps against contact with water.

8. A shower having a translucent wall and a device for installation behind the translucent wall of the shower, said device comprising a support assembly including means for mounting at least one source of ultraviolet radiation, guide means attachable to a fixed structure, and means for mounting the support assembly from the guide means such that the radiation source is positioned to direct radiation into the shower through the wall, said assembly being movable along the guide means to permit the assembly to be at least partially withdrawn from behind the wall to permit access to the assembly.

9. A shower according to claim 8, wherein the support assembly comprises means for mounting a plurality of tubular ultraviolet lamps, and reflector means positioned to reflect radiation from the lamps into the shower.

* * * * *